(12) United States Patent
Filippi et al.

(10) Patent No.: US 6,946,494 B2
(45) Date of Patent: Sep. 20, 2005

(54) PROCESS AND PLANT FOR THE HETEROGENEOUS SYNTHESIS OF CHEMICAL COMPOUNDS

(75) Inventors: Ermanno Filippi, Castagnola (CH); Enrico Rizzi, Grandate (IT); Mirco Tarozzo, Ligornetto (CH)

(73) Assignee: Methanol Casale S.A. (CH)

( * ) Notice: Subject to any disclaimer, the term of this patent is extended or adjusted under 35 U.S.C. 154(b) by 6 days.

(21) Appl. No.: 10/471,350

(22) PCT Filed: Oct. 2, 2002

(86) PCT No.: PCT/EP02/11027

§ 371 (c)(1),
(2), (4) Date: Sep. 8, 2003

(87) PCT Pub. No.: WO03/042143

PCT Pub. Date: May 22, 2003

(65) Prior Publication Data

US 2004/0204507 A1 Oct. 14, 2004

(30) Foreign Application Priority Data

Nov. 11, 2001 (EP) .............................................. 01126840

(51) Int. Cl.[7] .............................. C07C 27/00; C01C 1/00

(52) U.S. Cl. ....................... 518/706; 518/700; 518/705; 518/712; 423/352

(58) Field of Search ................................ 518/700, 705, 518/706, 712; 423/352

(56) References Cited

U.S. PATENT DOCUMENTS 4,559,207 A 12/1985 Hiller et al.
5,827,901 A 10/1998 Konig et al.

FOREIGN PATENT DOCUMENTS

GB 2 203 427 A 10/1988

*Primary Examiner*—J. Parsa
(74) *Attorney, Agent, or Firm*—Akerman Senterfitt

(57) ABSTRACT

A process for the heterogeneous synthesis of chemical compounds such as methanol and ammonia through catalytic conversion of the respective gaseous reactants that are made to pass through a first (2) and a second (3) reaction zone connected in series with each other, in which they react in pseudoisothermal conditions, distinguishes itself in that in the first reaction zone (2) the gaseous reactants are made to flow through a fixed mass of an appropriate catalyst in which a plurality of substantially box-like, plate-shaped heat exchangers (21), arranged side-by-side and crossed by a heat exchange operating fluid, is dipped.

5 Claims, 2 Drawing Sheets

PROCESS AND PLANT FOR THE HETEROGENEOUS SYNTHESIS OF CHEMICAL COMPOUNDS

FIELD OF APPLICATION

The present invention relates, in its broader aspect, to a process for the heterogeneous synthesis of chemical compounds such as methanol and ammonia.

In particular, the present invention relates to a process of the type comprising two reaction zones connected in series with each other in order to carry out catalyzed chemical reactions in so called pseudoisothermal conditions, wherein the reaction temperature is controlled within a restricted range of values around a predetermined optimal value.

The present invention also relates to a plant for carrying out the aforesaid process.

PRIOR ART

In the field of the industrial production of chemical compounds such as methanol and ammonia, the need is well known of developing processes of heterogeneous synthesis with a high conversion yield of the reactants and plants with large capacities, at low investment costs and energy consumption.

In order to fulfil the aforesaid need, a process for methanol synthesis has been proposed in the art, comprising two reaction zones connected in series with each other and operating in pseudoisothermal conditions, i.e. with reaction heat removal, wherein the heat in excess formed in the second reaction zone is removed by indirect heat exchange with the flow of fresh and recycled reactants fed into the first reaction zone.

Such process is described in EP-A-0 790 226. In order to operate correctly and reach the desired economical advantages, it is however necessary that the first reaction zone be consisting of a tube bundle exchanger, with the corresponding tubes filled with a suitable catalyst. The tubes are internally crossed by the gaseous reactants $H_2$ and CO, whereas externally they are licked by a water flow (with steam production) as heat exchange operating fluid. A reactor of this type is for example described in U.S. Pat. No. 4,559,207.

The need to employ this specific kind of reactor in the first reaction zone of a two-step process for the synthesis of methanol is also confirmed in GB-A-2 203 427.

Although advantageous under various aspects, the above described process has a relevant and acknowledged technical drawback, which constitutes, at an industrial level, a sure limit for the advancement or completion degree of the chemical reaction considered (conversion yield) as well as of the productive capacity of the respective plant.

In fact, the tube bundle reactors just described imply a complexity of structure and use such as to only allow the manufacture of rather small reaction volumes as clearly indicated in EP-A-0 790 226, with the disadvantage of impairing the conversion yield and the productive capacity that can be obtained by such reactors.

For larger reaction volumes the tube bundle reactors, besides being of very difficult if not impossible application, require such a high amount of investments that the process with a two-step reaction is no longer cost-effective.

In order to overcome such drawback, GE-A-2 203 427 proposes to use a high efficiency catalyst, which, besides solving only partially the problem of the low conversion and production yield in the tube bundle reactors, is however very expensive.

As a result, because of the aforesaid disadvantages, the processes according to the prior art do not allow to obtain in a relatively cost-effective and technically simple and reliable way, high conversion yields and high production capacities.

SUMMARY OF THE INVENTION

The technical problem underlying the present invention is that of providing a process for the heterogeneous synthesis of chemical compounds such as methanol and ammonia, which is easy to develop and allows high conversion yields to be obtained in chemical plants with large capacities at low investment costs and energy consumption, overcoming the drawbacks of the prior art.

The above indicated technical problem is solved, according to the invention, by a process for the heterogeneous synthesis of chemical compounds such as methanol and ammonia through catalytic conversion of the respective gaseous reactants that are made to cross through a first and a second reaction zone connected in series with each other in which they react in pseudoisothermal conditions, which process is characterized by the fact that in said first reaction zone the gaseous reactants are made to flow through a fixed mass of an appropriate catalyst in which a plurality of substantially box-like, plate-shaped heat exchangers, arranged side-by-side and crossed by the heat exchange operating fluid, is dipped.

Advantageously, contrary to the constant teaching of the prior art, it has been surprisingly found that the conversion yield and the production capacity of the first reaction zone in a process of the above described type can be remarkably increased, in a simple, reliable and cost-effective way, thanks to the aforesaid features.

In doing so, it is possible to produce the aforesaid chemical compounds in large amounts and with a high conversion yield in large capacity chemical plants, which are technically simple to be developed and do not imply high energy consumption and high investment and maintenance costs.

The invention further relates to a chemical plant having structural and functional features suitable to carry out the aforesaid process.

The features and advantages of the process according to the invention will be clearer from the description of an indicative and not-limiting embodiment thereof, made with reference to the attached drawings.

DETAILED DESCRIPTION OF THE DRAWINGS

Figure 1:
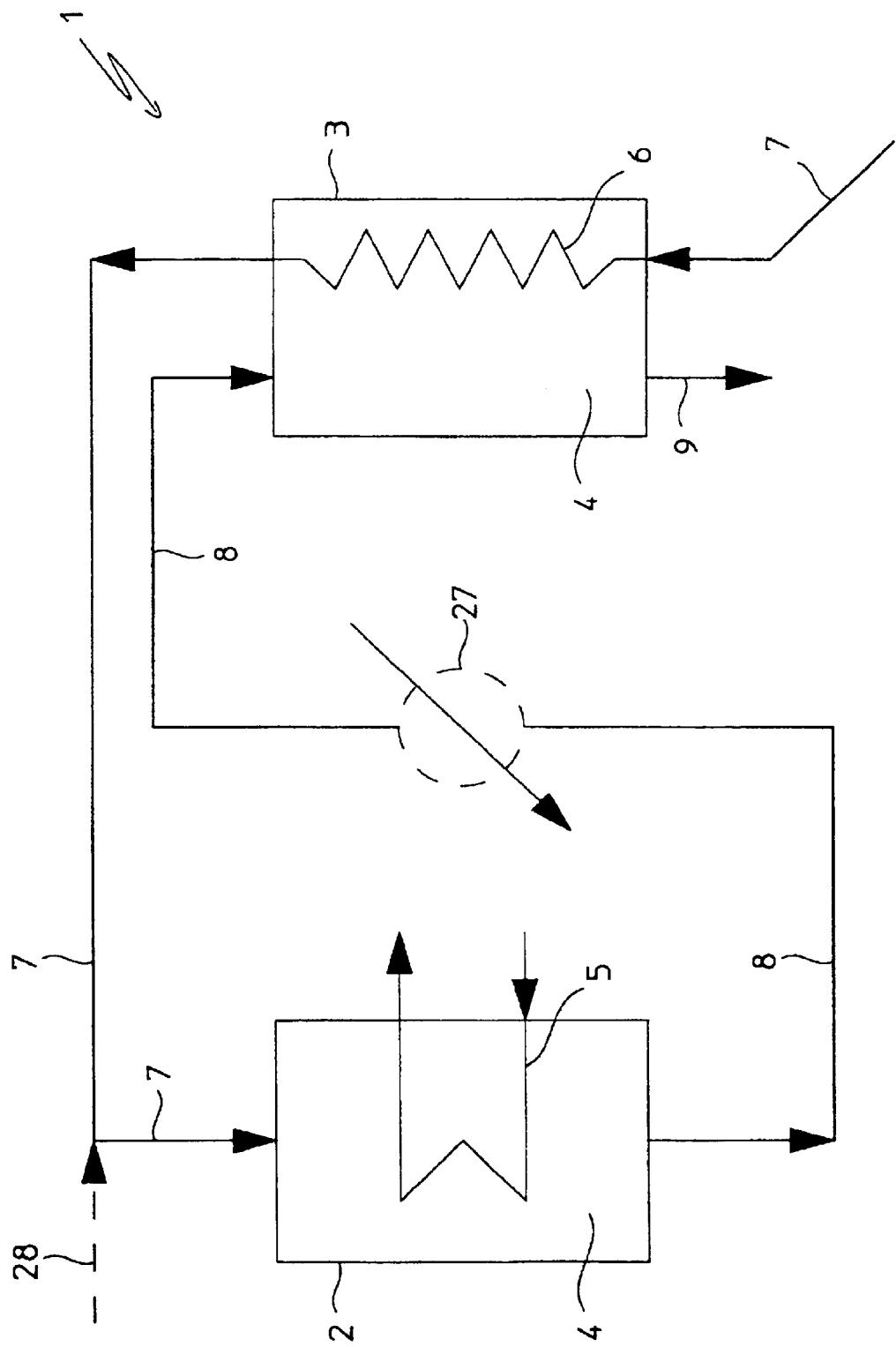
FIG. 1 shows in a general and schematic way a block diagram illustrating a plant for carrying out the process according to an embodiment of the present invention.

In FIG. 1 there is schematically illustrated in all of its main components a plant for methanol or ammonia production according to the present invention, which is indicated in its whole with numeral 1.

Plant 1 comprises a first reaction zone 2 and a second reaction zone 3, connected in series with each other.

Inside the reaction zones 2 and 3, a reaction area 4 is provided to house, in a per se known way, a fixed mass of a suitable catalyst, not shown.

The reaction zones 2 and 3, when in function, do operate in pseudoisothermal conditions and therefore are equipped with heat exchange units 5 and 6, respectively, dipped into said catalyst in the reaction area 4.

The reaction temperature inside the area 4 of the first reaction zone 2 is controlled through indirect heat exchange by making a heat exchange fluid to flow inside the unit 5, as indicated by the arrows. A heat exchange fluid such as for example water in case of exothermal reactions, such as methanol or ammonia synthesis. During such crossing, the water is transformed into steam or is simply preheated for the following production of steam in dedicated boilers placed outside the reaction zone and not shown.

The reaction temperature inside the area 4 of the second reaction zone 3 is instead controlled by indirect heat exchange, by making a flow of gaseous reactants, for feeding into the first reaction zone 2, to flow inside the heat exchange unit 6 as heat exchange fluid. In this respect, a pipe 7, in fluid communication with the heat exchange unit 6, enters into the second reaction zone 3 at such unit 6, then comes out of the same and enters into the first reaction zone 2 in the reaction area 4.

The pipe 7, as well as the unit 6, is crossed by a flow of gaseous reactants, such as $H_2$ and CO for methanol synthesis and $H_2$ and $N_2$ for ammonia synthesis, both fresh and recycled.

Furthermore, a pipe indicated with numeral 8 puts in fluid communication the outlet of the area 4 of the first reaction zone 2 with the inlet of the area 4 of the second reaction zone, for feeding thereto a reaction mixture comprising methanol or ammonia and unreacted gaseous reactants obtained in the first reaction zone 2.

Exiting from the area 4 of the second reaction zone 3, a pipe 9 is finally arranged for the outlet of the end reaction mixture, comprising also a portion of unreacted gaseous reactants beside methanol or ammonia.

In a section of the plant of FIG. 1 in fluid communication with the pipe 9 and not shown as it is per se conventional, the methanol and ammonia so obtained are separated from the reaction mixture and the gaseous reactants present in such mixture are recycled into the first reaction zone 2 through the pipe 7 together with the fresh feed gaseous reactants.

Figure 2:
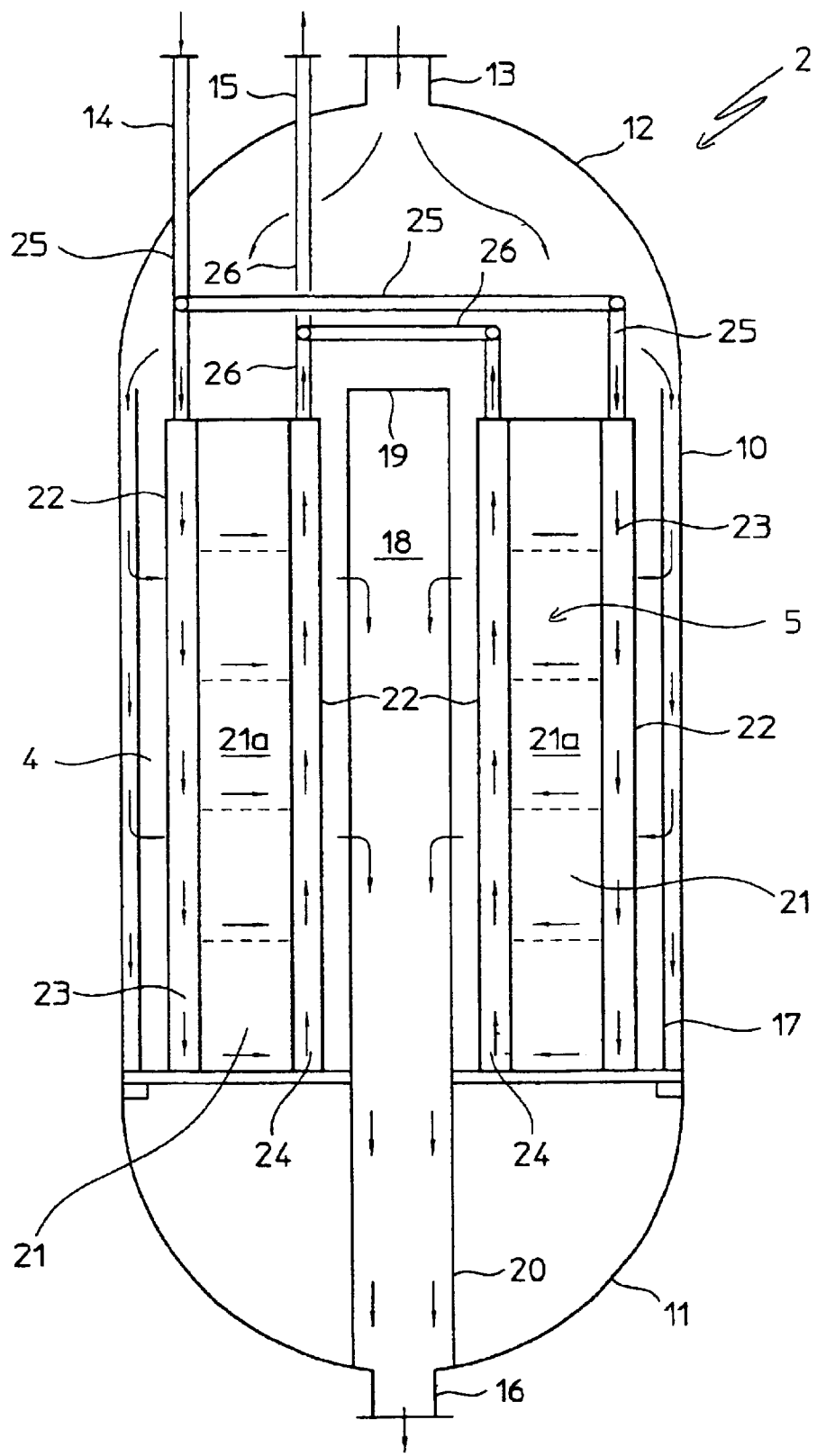
FIG. 2 schematically shows in longitudinal section a detail of the plant represented by the block diagram of FIG. 1.

According to a feature of the present invention, the heat exchange unit 5, besides being dipped into the catalyst of the reaction area 4, is made up of a plurality of substantially box-like, plate-shaped heat exchangers, arranged side-by-side and crossed by the heat exchange operating fluid, as can be seen in FIG. 2 which represents in greater detail the first reaction zone 2.

In such figure, the first reaction zone 2 consists of a pseudoisothermal reactor comprising a cylindrical shell 10, closed at the opposite ends by respective upper 11 and lower 12 bottoms and enclosing a heat exchange unit 5 provided with plate-shaped elements, which will be illustrated in the following description.

The upper bottom 12 is provided with a nozzle 13 for the inlet into the reactor 2 of the gaseous reactants coming from the pipe 7 of FIG. 1, and with nozzles 14, 15 for the inlet and outlet of the heat exchange operating fluid in and from the heat exchange unit 5, respectively.

The lower bottom 11 is instead equipped with a nozzle 16 for the outflow from the reactor 2 of the reaction mixture in fluid communication with the pipe 8 of FIG. 1.

Inside the shell 10 the reaction area 4 is provided, which comprises an annular catalytic bed 17, known per se, open above and with the side-walls perforated, for a radial or axial-radial crossing of the bed by the gaseous reactants.

The inner side-wall of the catalytic bed 17 forms in its interior a passage 18, closed above by a cover 19 and in fluid communication through a joint 20 with the nozzle 16 for the outlet of the reaction mixture.

In the reaction area 4, and more precisely inside the catalytic bed 17, the heat exchange unit 5 is supported, in a per se conventional way, to be dipped in the mass of an appropriate catalyst, not represented.

According to this embodiment, the heat exchange unit 5 has a substantially cylindrical configuration and comprises a plurality of flattened, substantially box-like, plate-shaped heat exchangers 21 with a parallelepiped configuration, placed side-by-side in an arrangement with coaxial and concentric elements (substantially radial arrangement).

More in particular, although not represented, each heat exchanger 21 is preferably made up of a pair of juxtaposed metallic plates mutually joined in a predetermined distanced relationship by perimetric soldering, so that a chamber 21a (illustrated with a dotted line) is defined between them, intended for being crossed by the heat exchange operating fluid.

Each heat exchanger 21 is provided, at its opposite long sides 22, with a distribution pipe 23 and a collector pipe 24, respectively, for said operating fluid. The pipes 23 and 24 are in fluid communication, on one side, with said chamber 21a through at least one, but preferably through a plurality of openings or holes (not represented), of which they are provided with along one or more generatrices and, on the other side, with the space outside the exchanger 21 through respective inlet and outlet tubular joints 25 and 26, for said operating fluid. The joints 25 and 26 are in turn connected with the nozzles 14 and 15, respectively.

In order to facilitate the crossing by the heat exchange operating fluid of the heat exchanger 6 in radial or substantially radial direction, the chamber 21a is preferably divided into a plurality of partitions, not directly in communication with each other and obtained, for example, through a corresponding plurality of welding seams or separating baffles (indicated with a dotted line) extending perpendicularly to the distributing pipe 23 and to the collector pipe 24 of the exchanger 21.

Thanks to this embodiment of the first reaction zone 2, it is possible to carry out the process according to the present invention, in which the gaseous reactants are made to flow through a fixed mass of a suitable catalyst of such reaction area, in which a plurality of substantially box-like, plate-shaped heat exchangers, arranged side-by-side and crossed by the heat exchange operating fluid, is dipped.

In doing so, it is advantageously possible to develop in a simple, reliable, and economic way and with low energy consumption even large spaces (volumes) of reaction for the first reaction zone 2.

In other words, the presence of plate-shaped heat exchangers dipped into the catalytic mass, besides being particularly effective as indirect heat exchange elements, allow the sizing of the first reaction zone 2 to be carried out at will, and thus to obtain in such reaction zone a high conversion yield and a high production capacity, to the advantage of the global conversion yield as well as to the development of plants with a large capacity.

The invention thus conceived may be susceptible to variations and modifications, all falling within the scope of protection defined in the following claims.

For example, according to a preferred embodiment of the present invention, the reaction mixture coming from the first reaction zone 2 and fed to the second reaction zone 3 through the pipe 8, is advantageously cooled by means of indirect heat exchange in a heat exchanger 27—of the conventional type—illustrated with a dotted line in FIG. 1. In this way, not only is it possible to recover heat in order to produce, for example, steam to be used in other parts of the steam plant but, above all, it is possible to control the inlet temperature to the second reaction zone 3 and hence its conversion yield.

Alternatively, it is also possible to foresee that a part of the "fresh" gaseous reactants and/or of the recycled reactants be directly fed to the first reaction zone 2, through a pipe 28, without passing through the second reaction zone 3.

The heat exchange unit 6 may be of a conventional type, i.e. of the tube bundle type or else in the form of a serpentine pipe, or, advantageously it can also be made up of a plurality of plate-shaped heat exchangers of the type described with reference to FIG. 2. In doing so, it is possible to obtain a further increase of the conversion yield and of the production capacity of the chemical plant.

According to a further embodiment of the invention, not represented, the first and the second reaction zone 2, 3 may be enclosed in a single synthesis reactor, instead of having two reactors as in the example of FIG. 1.

The operating conditions of temperature inside the reaction zones are the conventional ones for methanol or ammonia synthesis. As far as the pressure operating conditions are concerned, particularly satisfying results have been obtained by operating the two reaction zones 2 and 3 substantially at the same pressure, and preferably between 50 and 100 bars for the methanol synthesis and between 50 and 300 bars, preferably between 80 and 150 bars, for ammonia synthesis.

What is claimed is:

1. A process for the heterogeneous synthesis of methanol or ammonia through catalytic conversion of the respective gaseous reactants comprising the steps of passing the gaseous reactants through a first and a second reaction zone connected in series with each other, in which the gaseous reactants react in pseudoisothermal conditions, and causing, in said first reaction zone, the gaseous reactants to flow through a fixed mass of an appropriate catalyst in which a plurality of substantially box-like, plate-shaped heat exchangers arranged side-by-side and crossed by a heat exchange operating fluid, is dipped.

2. The process according to claim 1, wherein the pressure inside said reaction zones is the same.

3. The process according to claim 1, wherein said gaseous reactants are fed into said first reaction zone after indirect heat exchange inside said second reaction zone with a reaction mixture fed into this latter reaction zone and coming from said first reaction zone.

4. The process according to claim 1, wherein said second reaction zone is fed with a reaction mixture coming from said first reaction zone and subjected beforehand to indirect heat exchange in order to control its inlet temperature into said second zone.

5. The process according to claim 1, wherein said first reaction zone is fed with a mixture of gaseous reactants comprising fresh gaseous reactants and recycled gaseous reactants, the latter being suitably separated by a reaction mixture coming from said second reaction zone.

* * * * *